US012687545B2

(12) United States Patent
Lee et al.

(10) Patent No.: US 12,687,545 B2
(45) Date of Patent: Jul. 21, 2026

(54) FLUORESCENT PROTEIN SENSOR CAPABLE OF QUANTITATIVELY MEASURING OXIDATION DEGREE OF METHIONINE RESIDUES OF SPECIFIC PROTEIN, AND USE THEREOF

(71) Applicant: GERONMED, CO. LTD, Seoul (KR)

(72) Inventors: Byung Cheon Lee, Seoul (KR); Hae Min Lee, Seoul (KR)

(73) Assignee: GERONMED, CO. LTD, Seoul (KR)

( * ) Notice: Subject to any disclaimer, the term of this patent is extended or adjusted under 35 U.S.C. 154(b) by 699 days.

(21) Appl. No.: 18/029,086

(22) PCT Filed: Sep. 28, 2021

(86) PCT No.: PCT/KR2021/013211
§ 371 (c)(1),
(2) Date: Jun. 27, 2023

(87) PCT Pub. No.: WO2022/065974
PCT Pub. Date: Mar. 31, 2022

(65) Prior Publication Data
US 2023/0375562 A1 Nov. 23, 2023

(30) Foreign Application Priority Data
Sep. 28, 2020 (KR) ........................ 10-2020-0126105

(51) Int. Cl.
*G01N 33/68* (2006.01)
*C07K 14/315* (2006.01)
*C07K 14/35* (2006.01)

(52) U.S. Cl.
CPC ....... *G01N 33/6815* (2013.01); *C07K 14/315* (2013.01); *C07K 14/35* (2013.01); *C07K 2319/60* (2013.01); *G01N 2800/7009* (2013.01)

(58) Field of Classification Search
CPC ....... G01N 33/6815; G01N 2800/7009; G01N 33/582; G01N 2500/00; G01N 33/6893;
(Continued)

(56) References Cited

U.S. PATENT DOCUMENTS

2004/0137643 A1* 7/2004 Humphreys ......... G01N 33/533
436/518

FOREIGN PATENT DOCUMENTS

| CN | 102094068 | 6/2011 |
| CN | 111458435 | 7/2020 |
| WO | 2019203248 | 10/2019 |

OTHER PUBLICATIONS

Lionel Tarrago et al., "Supplementary information: Monitoring methionine sulfoxide with stereospecific mechanism-based fluorescent sensors", Nature Chemical Biology, vol. 11, No. 5, May 1, 2015, pp. 1-21.
"Search Report of Europe Counterpart Application", issued on Sep. 16, 2024, p. 1-p. 7.
"Office Action of Korea Counterpart Application", issued on Oct. 18, 2022, with English translation thereof, p. 1-p. 2.
Biowave, vol. 20, No. 7, available at: www.ibric.org/myboard/read.php?Board=biolab&id=2609, published on Jul. 2018, pp. 1-3.
(Continued)

*Primary Examiner* — Brian J. Sines
(74) *Attorney, Agent, or Firm* — JCIPRNET

(57) ABSTRACT

A fluorescent protein sensor capable of quantitatively measuring oxidation degree of methionine residues of a specific protein, and a use thereof. Specifically, a fluorescent biosensor recombinant protein in which an MsrB protein, a cpYFP protein, a thioredoxin 3 protein, a linker protein and a G protein are linked in this order, and which is capable of quantitatively measuring the oxidation degree of methionine residues of a target protein; a fluorescent biosensor comprising same; a method for measuring oxidation degree of methionine residues of a target protein; and an information providing method for diagnosis of oxidative stress-associated diseases; and a method for screening for a therapeutic agent for oxidative stress-associated diseases. A recombinant protein for a fluorescent biosensor for accurately and quantitatively measuring, through the detection of a specific
(Continued)

Cys69  Cys129          Ser129  Cys417 change in fluorescence, oxidation degree of methionine residues of a specific protein, but not all proteins, even in a mixed biological sample.

17 Claims, 12 Drawing Sheets

Specification includes a Sequence Listing.

(58) Field of Classification Search
CPC .. G01N 21/6428; G01N 33/53; C07K 14/315; C07K 14/35; C07K 2319/60; C07K 2319/70; C07K 14/39; C07K 14/43595; C07K 2319/00; C12N 9/0051; C12N 15/70; C12N 15/62; C12Y 108/04012
See application file for complete search history.

(56) References Cited

OTHER PUBLICATIONS

Lionel Tarrago et al., "Monitoring methionine sulfoxide with stereospecific mechanism-based fluorescent sensors," Nature Chemical Biology, vol. 11, Mar. 2015, pp. 1-9.
Zalán Peterfi et al., "Practical guide for dynamic monitoring of protein oxidation using genetically encoded ratiometric fluorescent biosensors of methionine sulfoxide," Methods, vol. 109, Jun. 2016, pp. 149-157.
Dong Wook Choi et al., "Development of a novel fluorescent biosensor for dynamic monitoring of metabolic methionine redox status in cells and tissues," Biosensors and Bioelectronics, vol. 178, Jan. 2021, pp. 1-9.

* cited by examiner

ABSORPTION SPECTRUM
(340 nm to 700 nm)
OF FLUORESCENT BIO-SENSOR

CHANGE IN EXCITATION
SPECTRUM VALUE ($F_{500nm}/F_{415nm}$)
OF FLUORESCENT BIO-SENSOR ACCORDING
TO OXIDATION AND REDUCTION

RESULTS OF ELISA EXPERIMENTS USING FLUORESCENT
BIO-SENSOR WITH PURIFIED METHIONINE-CONTAINING PROTEINS
$(F_{500nm}/F_{415nm})$

ELISA RESULTS USING
FLUORESCENT BIO-SENSOR
FOR CALMODULIN IN Raw264.7 CELLS
$(F_{500nm}/F_{415nm})$

Normalized
fluorescence
ratio
$(F_{500nm}/F_{415nm})$

HYDROGEN PEROXIDE CONCENTRATION
TREATED TO CELLS

ELISA RESULTS USING
FLUORESCENT BIO-SENSOR
FOR CALMODULIN IN Raw264.7 CELLS
$(F_{500nm}/F_{415nm})$

Normalized
fluorescence
ratio
$(F_{500nm}/F_{415nm})$

NaOCl CONCENTRATION
TREATED TO CELLS

ELISA RESULTS USING
FLUORESCENT BIO-SENSOR
FOR CALMODULIN IN U87MG CELLS
$(F_{500nm}/F_{415nm})$

Normalized
fluorescence
ratio
$(F_{500nm}/F_{415nm})$ 1.0

0.5

0.0

Control    15mM    30mM    45mM

HYDROGEN PEROXIDE CONCENTRATION
TREATED TO CELLS

ELISA RESULTS USING
FLUORESCENT BIO-SENSOR
FOR CALMODULIN IN U87MG CELLS
$(F_{500nm}/F_{415nm})$

Normalized
fluorescence
ratio
$(F_{500nm}/F_{415nm})$

NaOCl CONCENTRATION
TREATED TO CELLS

FLUORESCENT PROTEIN SENSOR CAPABLE OF QUANTITATIVELY MEASURING OXIDATION DEGREE OF METHIONINE RESIDUES OF SPECIFIC PROTEIN, AND USE THEREOF

TECHNICAL FIELD

The present disclosure relates to a fluorescent protein sensor that can quantitatively measure the oxidation degree of methionine residues in a specific protein, and use thereof.

BACKGROUND ART

Living organisms are always exposed to the risk of reactive oxygen species (ROS) generated by metabolic processes within the body or environmental stress. The problem of these ROS is that they damage the macromolecules in living bodies, causing the development of diseases or the acceleration of aging. Among these macromolecules, deoxyribonucleic acid (DNA), lipids, proteins, etc. are typically directly damaged by ROS.

One of the major causative agents of oxidative stress, ROS, is naturally produced as a byproduct of various cellular organelles' metabolic processes and enzyme reactions in normal cellular activities. In general, living bodies have corresponding antioxidation mechanisms to balance the generation of ROS. However, when aging or disease occurs, oxidative stress occurs due to a sudden increase in the generation of ROS or a failure of living bodies' anti-oxidation mechanisms to function properly, leading to the accumulation of damage to biological molecules caused by ROS. When biological molecules such as DNA, proteins, and lipids are damaged by oxidative stress, it can lead to exacerbation of aging or disease, and therefore the levels of ROS within the body are crucial information for diagnosis and tracking of various diseases such as cancer or cardiovascular diseases, as well as aging.

Therefore, research on technologies for measuring the amounts of ROS within living bodies has been conducted, and methods using fluorescent dyes such as dichlorodihydrofluorescein diacetate (DCFDA) and dihydroethidium (DHE) staining have been developed. However, since ROS are generated momentarily and immediately react with other macromolecules in living bodies, there are limitations to directly measuring the amounts of ROS in general biological samples, except for living cells.

Another method in development is to measure the accumulation of substances that are oxidized by ROS, and methionine in particular is an amino acid that is relatively easily oxidized compared to other amino acids because it has a sulfur atom in its side chain. For this reason, methionine always plays a frontline role in the battle against ROS, and since it is not free to undergo protein modification and functional loss due to its susceptibility to oxidation, research has been developed to indirectly confirm the amounts of ROS by measuring the oxidation degrees of methionine residues.

However, the conventionally developed measurement of the oxidative degree of methionine residues has been to measure the overall oxidative degree of methionine residues in all proteins within living bodies. Therefore, there are currently no techniques available to directly measure the oxidative degrees of methionine residues in specific proteins.

DISCLOSURE

Technical Problem

Accordingly, the inventors of the present application have completed the present disclosure by developing a novel fluorescent protein sensor based on a biological protein that can accurately measure the oxidation degree of methionine residues occurring in a specific protein targeted by reactive oxygen species (ROS) with high specificity and sensitivity.

Therefore, the objective of the present disclosure is to provide a recombinant protein for use in a fluorescent bio-sensor that can measure the oxidation degree of methionine residues in a target protein.

Another objective of the present disclosure is to provide a polynucleotide encoding the recombinant protein for a fluorescent bio-sensor of the present disclosure.

Another objective of the present disclosure is to provide an expression vector including the polynucleotide of the present disclosure.

Another objective of the present disclosure is to provide a transgenic organism that has been transformed with the expression vector of the present disclosure.

Another objective of the present disclosure is to provide a fluorescent bio-sensor capable of measuring the oxidation degree of methionine residues in the target protein, including the recombinant protein for a fluorescent bio-sensor of the present disclosure.

Another objective of the present disclosure is to provide a composition for quantitative detection of the oxidation degree of methionine residues in a target protein.

Another objective of the present disclosure is to provide a method of measuring the oxidation degree of methionine residues in a target protein using the recombinant protein for a fluorescent bio-sensor according to the present disclosure.

Another objective of the present disclosure is to provide a method of providing information for diagnosing oxidative stress-related diseases using the recombinant protein for a fluorescent bio-sensor according to the present disclosure.

Another objective of the present disclosure is to provide a method of screening therapeutic agents for oxidative stress-related diseases using the recombinant protein for a fluorescent bio-sensor according to the present disclosure.

Technical Solution to Problem

Therefore, the present disclosure provides a recombinant protein for a fluorescent bio-sensor capable of measuring the oxidative degree of methionine residues in a target protein, which is sequentially linked with methionine sulfoxide reductase B (MsrB) protein; circularly permuted yellow fluorescent protein (cpYFP); thioredoxin 3 protein; linker protein; and Protein G.

According to an embodiment of the present disclosure, the recombinant protein for a fluorescent bio-sensor may consist of an amino acid sequence of SEQ ID NO: 2.

According to an embodiment of the present disclosure, the MsrB protein may consist of $1^{st}$ to $139^{th}$ amino acids of the amino acid sequence of SEQ ID NO: 2, the cpYFP may consist of $140^{th}$ to $381^{th}$ amino acids of the amino acid sequence of SEQ ID NO: 2, the thioredoxin 3 protein may consist of $382^{th}$ to $488^{th}$ amino acids of the amino acid sequence of SEQ ID NO: 2, the linker protein may consist of $489^{th}$ to $521^{th}$ amino acids of the amino acid sequence of SEQ ID NO: 2, and the Protein G may consist of $522^{th}$ to $575^{th}$ amino acids of the amino acid sequence of SEQ ID NO: 2.

In addition, the present disclosure provides a polynucleotide encoding the recombinant protein for a fluorescent bio-sensor of the present disclosure.

According to an embodiment of the present disclosure, the polynucleotide may consist of a nucleotide sequence of SEQ ID NO: 1.

According to an embodiment of the present disclosure, of the nucleotide sequence of SEQ ID NO: 1, the nucleotide sequence that codes for the MsrB protein may consist of $1^{st}$ to $417^{th}$ nucleotides, the nucleotide sequence that codes for the cpYFP may consist of $418^{th}$ to $1143^{th}$ nucleotides, the nucleotide sequence that codes for the thioredoxin 3 protein may consist of $1144^{th}$ to $1464^{th}$ nucleotides, the nucleotide sequence that codes for the linker protein may consist of $1465^{th}$ to $1563^{th}$ nucleotides, and the nucleotide sequence that codes for the Protein G may consist of $1564^{th}$ to $1725^{th}$ nucleotides.

In addition, the present disclosure provides an expression vector including the polynucleotide of the present disclosure.

In addition, the present disclosure provides transgenic organism transformed with the expression vector of the present disclosure.

In addition, the present disclosure provides a fluorescent bio-sensor capable of measuring the oxidation degree of methionine residues in a target protein, including the recombinant protein for a fluorescent bio-sensor of the present disclosure.

In addition, the present disclosure provides a composition for quantitative detection of the oxidation degree of methionine residues in the target protein, including the recombinant protein for a fluorescent bio-sensor of the present disclosure and a primary antibody against the detection target protein.

In addition, the present disclosure provides a method of measuring the oxidative degree of methionine residues in a target protein, including: (1) preparing a sample including the target protein with methionine residues; (2) treating the sample with a primary antibody against the target protein to bind the antibody to the target protein; (3) treating the sample with a recombinant protein for a fluorescent bio-sensor according to the present disclosure; and (4) measuring the fluorescent spectrum values of the recombinant protein for a fluorescent bio-sensor, included in the method of measuring the oxidative degree of the methionine residues in the target protein.

According to an embodiment of the present disclosure, the measurement of the fluorescence spectrum value may be calculated by the following Equation.

$$\frac{500 \text{ nm value of the excitation spectrum (fixed at 535 nm emission wavelength)}}{415 \text{ nm value of the excitation spectrum (fixed at 535 nm emission wavelength)}} = F_{500\,nm}/F_{415\,nm} \qquad \text{Equation}$$

According to an embodiment of the present disclosure, it may be that as the oxidation of methionine residues in the target protein increases, the numerical value of the fluorescence spectrum value may decrease.

In addition, the present disclosure provides a method of providing information for diagnosing oxidative stress-related diseases, including the processes of treating a biological sample isolated from a test subject with a detection composition of the present disclosure, and comparing the fluorescence spectrum value of the recombinant protein for a fluorescent bio-sensor with the fluorescence spectrum value of a normal control group, wherein the fluorescence spectrum value is calculated by Equation.

According to an embodiment of the present disclosure, the sample may be cells, tissue, blood, plasma, serum, saliva, or urine.

According to an embodiment of the present disclosure, the oxidative stress-related disease may be selected from a group consisting of cancer, stroke, myocardial infarction, angina pectoris, arteriosclerosis, infertility, hepatitis, osteoarthritis, cataracts, lipid metabolic syndrome, heart failure, hypertensive heart disease, arrhythmia, and aging.

In addition, the present disclosure provides a method of screening therapeutic agents for oxidative stress-related disorders, including: (1) inducing oxidative stress in a sample including a protein including methionine residues; (2) treating the sample with a candidate drug; and (3) treating the sample with the detection composition of the present disclosure, after the candidate compound has been treated, and comparing the fluorescence spectrum value of the recombinant protein for a fluorescence bio-sensor with the fluorescence spectrum value of the control group not treated with the candidate compound, wherein the fluorescence spectrum value is calculated by Equation.

According to an embodiment of the present disclosure, if the fluorescence spectrum value of the sample treated with the candidate drug is higher than the fluorescence spectrum value of the control group, the method may further include determining the candidate drug as a therapeutic agent for oxidative stress-related diseases.

According to an embodiment of the present disclosure, the oxidative stress-related disease may be selected from a group consisting of cancer, stroke, myocardial infarction, angina pectoris, arteriosclerosis, infertility, hepatitis, osteoarthritis, cataracts, lipid metabolic syndrome, heart failure, hypertensive heart disease, arrhythmia, and aging.

Advantageous Effects of Disclosure

A recombinant protein for a fluorescent bio-sensor according to the present disclosure can accurately and quantitatively measure the oxidation degree of methionine residues in a specific protein, rather than all proteins, even in mixed biological samples, by detecting specific fluorescent changes. Therefore, the recombinant protein for a fluorescent bio-sensor according to the present disclosure can be used as a fluorescent bio-sensor for the diagnosis of oxidative stress-related diseases, as well as in a screening method of therapeutic agents for oxidative stress-related diseases. In addition, it can be used in a method of diagnosing the state of the disease after drug treatment.

BRIEF DESCRIPTION OF DRAWINGS

FIGS. 2A-2C show the operating principle of a recombinant protein for a fluorescent bio-sensor according to the present disclosure, in which FIG. 2A shows a schematic representation of the recombinant protein for a fluorescent bio-sensor of the present disclosure, bound to the fragment crystallizable (Fc) region of an antibody in the presence of a target protein and its corresponding antibody, FIG. 2B shows the process in which the recombinant protein for a fluorescent bio-sensor of the present disclosure reduces methionine sulfoxide (MetO) of the target protein to methionine (Met), forming a disulfide bond between methionine sulfoxide reductase B1 (MsrB1) and thioredoxin 3 (Trx3) inside the recombinant protein, which affects the spectral properties of circularly permuted yellow fluorescence protein (cpYFP), and FIG. 2C shows the process of performing an enzyme-linked immunosorbent assay (ELISA) experiment using the characteristics of the recombinant protein for a fluorescent bio-sensor of the present disclosure.

FIGS. 3A-3D show the spectroscopic characteristics of a recombinant protein for a fluorescent bio-sensor of the present disclosure expressed in *Escherichia coli* (*E. coli*), including absorption spectrum, emission spectrum, and excitation spectrum, in which FIG. 3A shows the result of an absorption spectrum for the wavelength range of 340 nm to 700 nm, FIG. 3B shows the result of an emission spectrum of the recombinant protein for a fluorescent bio-sensor of the present disclosure in the oxidized (red line) and reduced (black line) states, measured in the wavelength range of 500 nm to 600 nm upon excitation at a wavelength of 410 nm, and FIG. 3C shows the result of an excitation spectrum of the recombinant protein for a fluorescent bio-sensor of the present disclosure in the oxidized (red line) and reduced (black line) states, measured in the wave length range of 360 nm to 520 nm, with the fixed emission wavelength of 535 nm, FIG. 3D shows a bar graph of the values obtained by dividing the value with the highest difference ($F_{500\ nm}$) by the value with the lowest difference ($F_{415\ nm}$) of an excitation spectrum for the oxidized and reduced forms of a reconstituted protein for a fluorescent bio-sensor of the present disclosure, based on the results of FIG. 3C, FIG. 3C shows an equation for a calculation method when the result of the excitation spectrum ($F_{500\ nm}/F_{415\ nm}$) is used as an indicator for detecting the oxidized state of the fluorescent bio-sensor of the present disclosure.

FIGS. 5A-5D show the results of excitation spectrum ($F_{500\ nm}/F_{415\ nm}$) of a recombinant protein for a fluorescent bio-sensor of the present disclosure, using calmodulin, one of the methionine-containing proteins, as a target protein, measured by ELISA with mixed biological samples, in which FIG. 5A is the result of an experimental group in which Raw264.7 cells were treated with hydrogen peroxide, FIG. 5B is the result of an experimental group in which in Raw264.7 cells were treated with NaOCl, FIG. 5C is the result of an experimental group in which U87MG cells were treated with hydrogen peroxide, and FIG. 5D is the result of an experimental group in which U87MG cells were treated with NaOCl.

BEST MODE

Figure 1:
FIG. 1 shows a schematic diagram of the genetic composition of a recombinant protein for a fluorescent bio-sensor of the present disclosure, which can quantitatively measure the oxidation degree of methionine residues in a specific protein, and a schematic diagram of the recombinant expression vector pBYTLG vector that includes the same.
Figure 1:
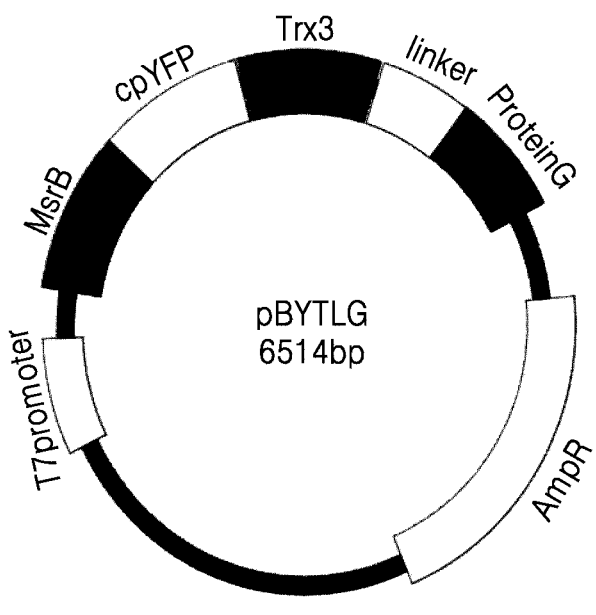

The present disclosure provides a novel fluorescent protein sensor capable of quantitatively measuring the oxidation of methionine in a specific single target protein within a living body due to oxidative stress, and specifically provides a recombinant protein for a fluorescent bio-sensor that can measure the degree of oxidation of methionine residues in the target protein, which is sequentially connected by methionine sulfoxide reductase B (MsrB) protein; circularly permuted yellow fluorescent protein (cpYFP); thioredoxin 3 (Trx 3) protein; linker protein and Protein G.

The oxidation of methionine in the target protein can be quantitatively measured by measuring fluorescent changes, using the recombinant protein for a fluorescent bio-sensor according to the present disclosure.

In the present disclosure, a recombinant protein for a fluorescent bio-sensor was produced to measure the oxidation of methionine residue in a specific protein. MsrB protein; cpYFP; thioredoxin 3 protein; linker protein and Protein G were sequentially fused to produce the recombinant protein.

The cpYFP is an artificially created protein by genetically manipulating a commonly known fluorescent protein, and cpYFP uses a principle of direct structural changes to vary the fluorescence value, which is different from the fluorescence resonance energy transfer (FRET) method, where two fluorophores emit light as their distance becomes farther and their influence decreases. Various bio-sensors are developed using this principle.

Therefore, in the present disclosure, a yeast or bacterial-like methionine sulfoxide reductase A (MsrA)/MsrB capable of reducing methionine sulfoxide (a product produced through the oxidation of methionine) is bound at one end of a circularly permuted yellow fluorescence protein (cpYFP), whose fluorescence value changes with structural changes, bound at the other end is a thioredoxin 3 protein, which is capable of reducing methionine sulfoxide and then returning MsrA/MsrB, which itself is oxidized, back to its reduced form. Thioredoxin 3 is then connected to a linker, and followed by connecting a *streptococcus*-derived Protein G.

Proteins with oxidized methionine are first reduced by MsrA/MsrB, followed by regeneration of MsrA/MsrB through disulfide bonds formation with thioredoxin 3, which is attached to the other end of cpYFP. At this time, the disulfide bond between MsrA/MsrB and thioredoxin generated during regeneration closes the distance between the two proteins, causing the fluorescence value of cpYFP in the middle to change. By measuring the change in fluorescence values, the amount of methionine oxide, that is, methionine sulfoxide, can be quantitatively measured.

Furthermore, the MsrB protein has the activity to reduce methionine-R-sulfoxide, an oxide of methionine in proteins. Following this reduction, Cys69 and Cys129 in the MsrB protein are oxidized to form a disulfide bond.

In addition, thioredoxin 3 acts to break disulfide bonds within the MsrB protein formed during the reduction of methionine-R-sulfoxide again through reduction. In more detail, Cys417 in the thioredoxin 3 protein attacks and reduces the disulfide bond, and a new disulfide bond is formed between Cys129 of MsrB and Cys417 of thioredoxin 3. Another Cys129 of the original thioredoxin 3 breaks the newly formed disulfide bond between MsrB and thioredoxin 3, completing the regeneration of MsrB. Genetic manipulation was used to replace Cys129 with Ser129 to prevent this from occurring. As a result, the disulfide bond between MsrB and thioredoxin 3 remains intact, and the structure of the cpYFP located in the middle can remain in its changed state. This, in turn, allows the change in fluorescence value of cpYFP to be maintained, allowing for the quantitative measurement of methionine oxide.

Furthermore, the linker protein between thioredoxin 3 and Protein G was produced to play a role of maintaining a sufficient distance between protein G and MsrB-cpYFP-Trx3, allowing MsrB stable access to the substrate. To this end, the linker amino acid sequence is inserted as a continuation of a sequence that does not form a secondary structure when the protein is subjected to folding.

Furthermore, Protein G is an immunoglobulin-binding protein, which has the ability to bind to antibodies. Protein G is a protein present in mammals such as humans and rats, mainly used to purify antibodies through binding to the fragment antigen binding (Fab) and fragment crystallizable (Fc) regions of antibodies (mainly immunoglobulin G (IgG) type) In the present disclosure, by using the Protein G, the recombinant protein for a fluorescent bio-sensor of the present disclosure specifically binds to an antibody bound to a specific protein to be detected so that the methionine oxide of the specifically bound protein can be quantitatively measured.

Figure 2A:
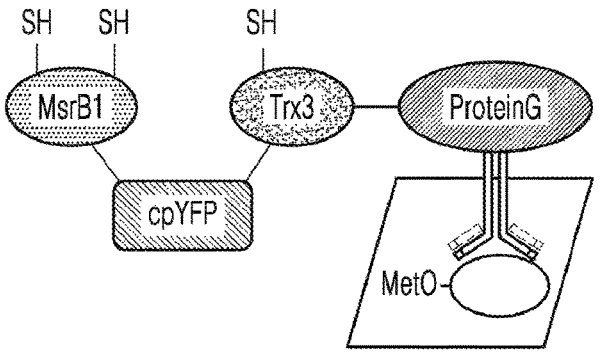
Figure 2B:
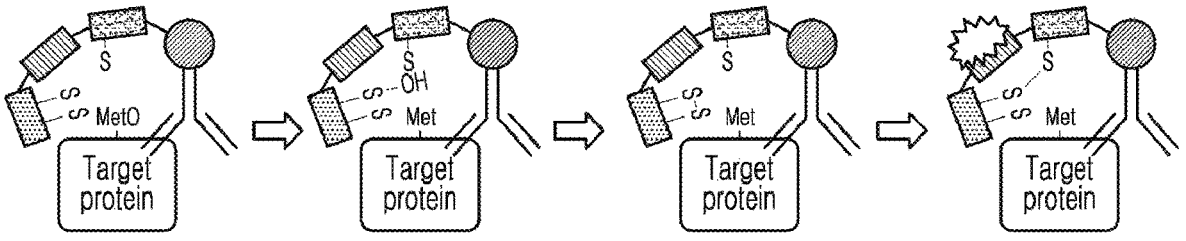
Figure 2C:
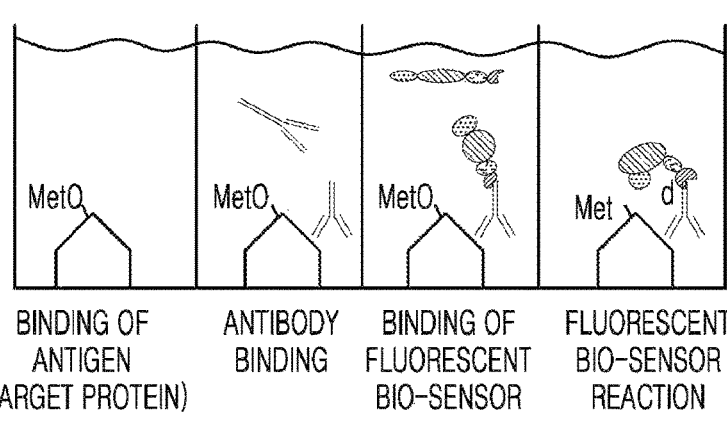
Figure 3A:
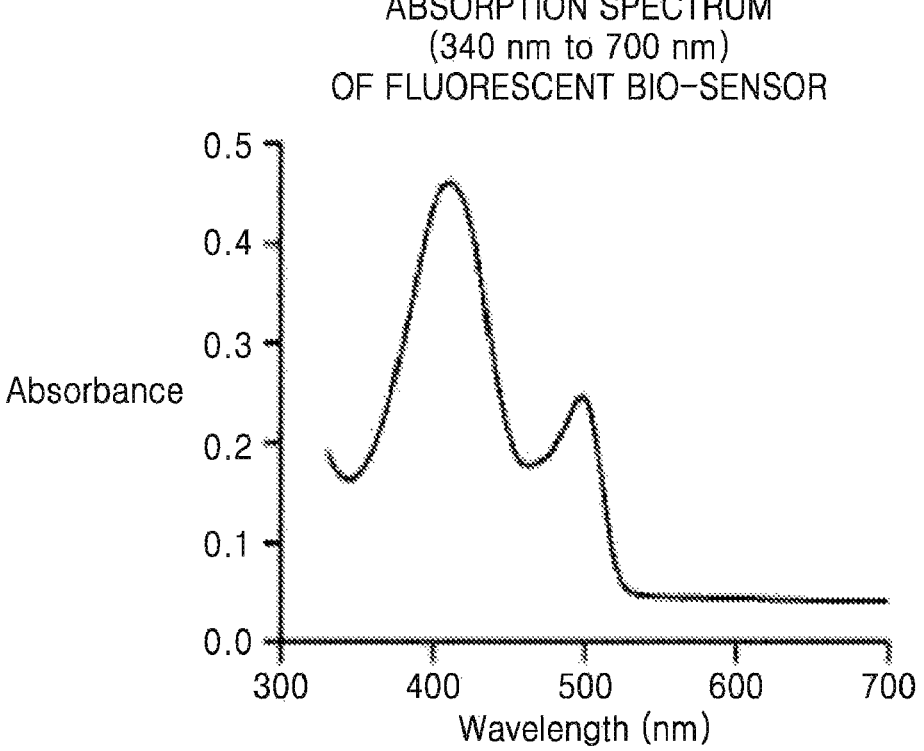
Figure 3B:
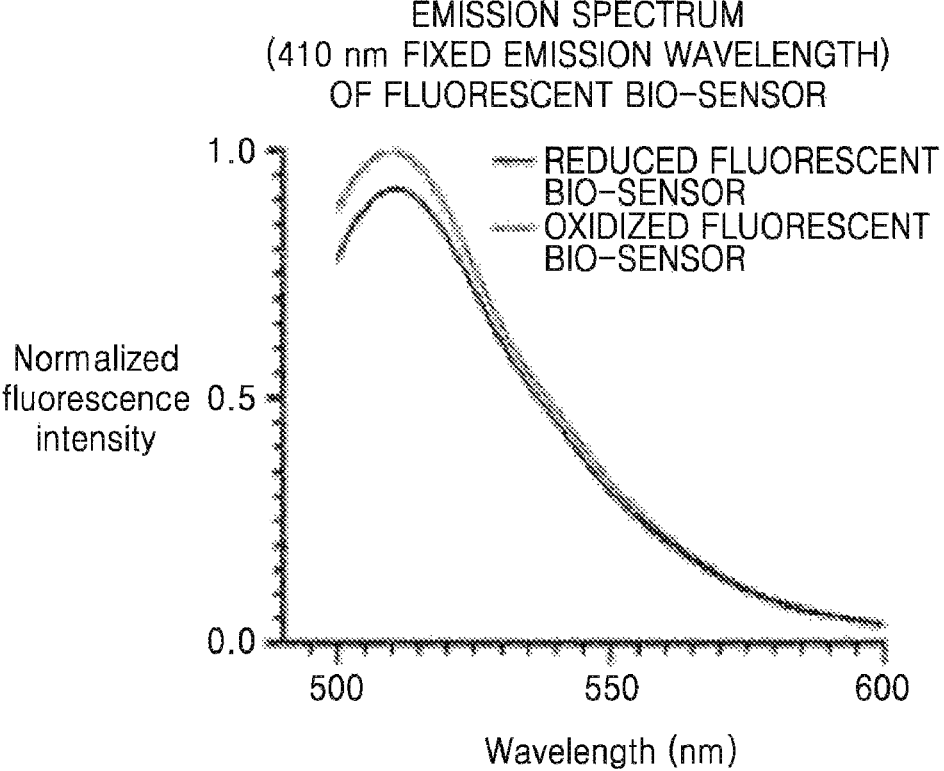
Figure 3C:
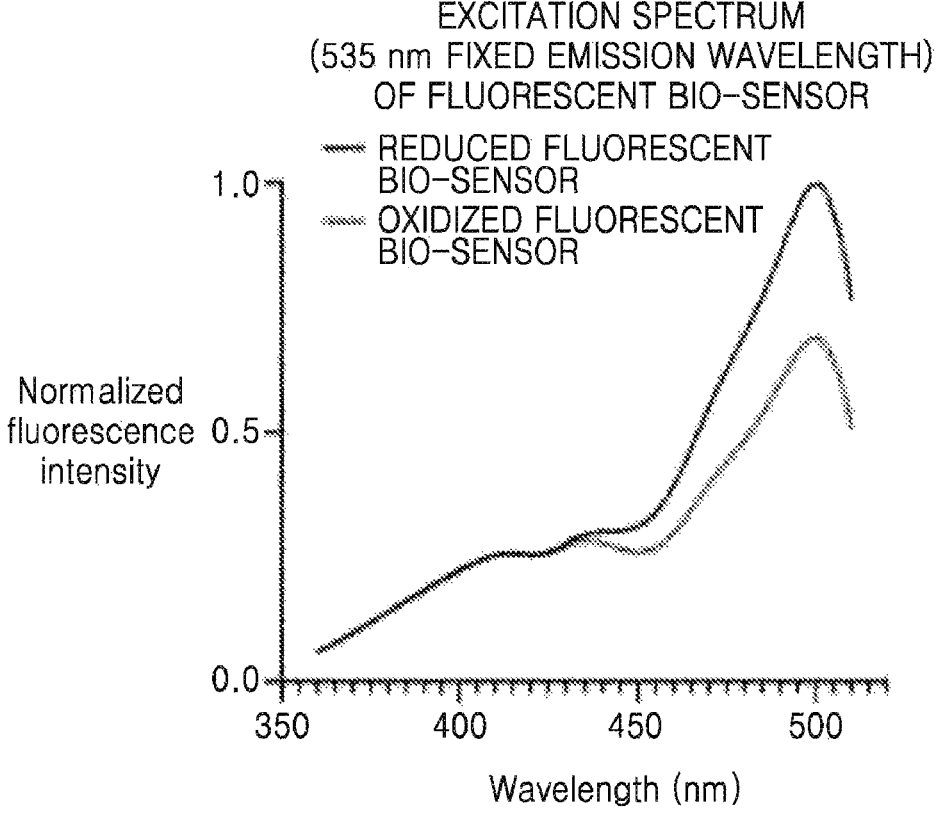
Figure 3D:
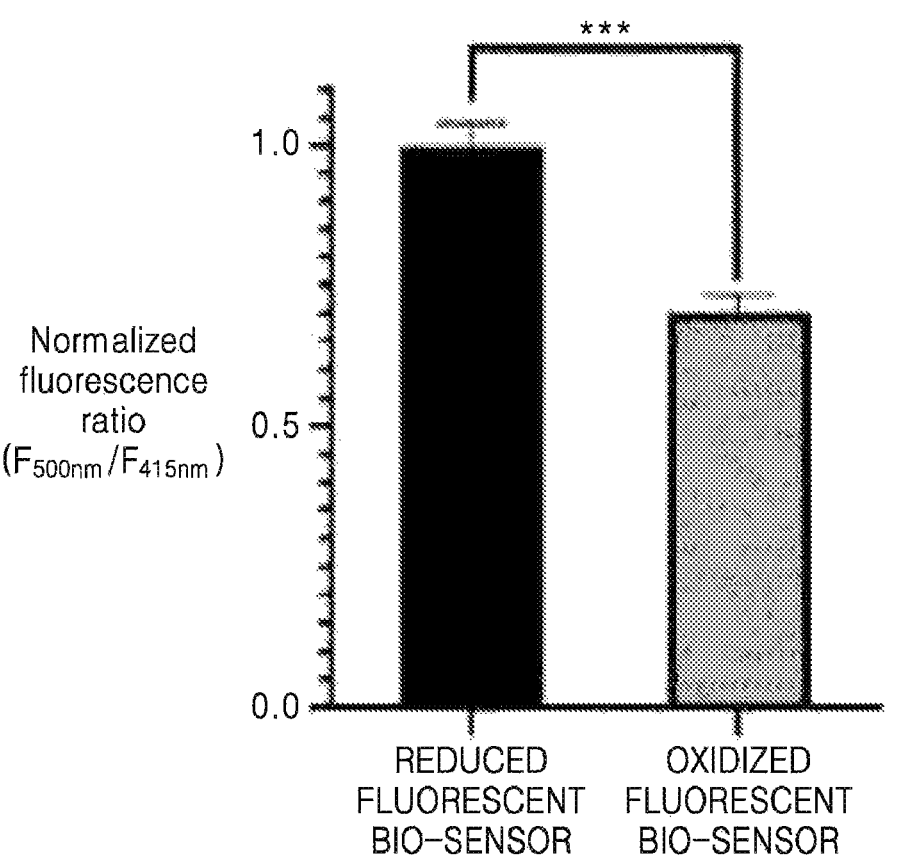

Shown in FIG. 2A to FIG. 2C, are the principles for quantifying methionine oxidation of a specific protein using a recombinant protein for a fluorescent bio-sensor according to the present disclosure.

Therefore, the present disclosure may provide a recombinant protein for a fluorescent bio-sensor capable of measuring the oxidation degree of methionine residues of a target protein, in which an MsrB protein; a cpYFP; a thioredoxin 3 protein; a linker protein and a Protein G are connected in sequence.

Preferably, the recombinant protein for a fluorescent bio-sensor of the present disclosure may include the amino acid sequence of SEQ ID NO. 2, wherein the MsrB protein may consist of $1^{st}$ to $139^{th}$ amino acids, and the cpYFP may consist of $140^{th}$ to $381^{th}$ amino acids, and the thioredoxin 3 protein may consist of $382^{th}$ to $488^{th}$ amino acids, and the linker protein may consist of $489^{th}$ to $521^{th}$ amino acids, and the Protein G may consist of $522^{th}$ to $575^{th}$ amino acids.

In addition, the present disclosure may provide a polynucleotide encoding a recombinant protein for a fluorescent bio-sensor of the present disclosure, preferably the polynucleotide may consist of the nucleotide sequence of SEQ ID NO: 1

In the sequence of SEQ ID NO: 1, a nucleotide sequence encoding the MsrB protein may consist of $1^{st}$ to $417^{th}$ nucleotides, and a nucleotide sequence encoding the cpYFP may consist of $418^{th}$ to $1143^{th}$ nucleotides, and a nucleotide sequence encoding the thioredoxin 3 protein may consist of $1144^{th}$ to $1464^{th}$ nucleotides, and a nucleotide sequence encoding the linker protein may consist of $1465^{th}$ to $1563^{th}$ nucleotides, and a nucleotide sequence encoding the Protein G may consist of $1564^{th}$ to $1725^{th}$ nucleotides.

In addition, the present disclosure may provide an expression vector including the polynucleotide, preferably the nucleotide sequence of SEQ ID NO: 1, and the term "expression vector" used herein refers to a member for expressing a recombinant protein by introducing deoxyribonucleic acid (DNA) into a host cell so as to prepare a transgenic organism expressing the recombinant protein of the present disclosure. For the expression vector, a plasmid vector, cosmid vector, bacteriophage vector, etc. may be used. In an embodiment, a plasmid vector may be used. According to the purpose of the present disclosure, expression vectors may include expression regulatory elements such as promoters, start codons, termination codons, polyadenylation signals, and enhancers.

According to an embodiment of the present disclosure, the recombinant expression vector "pBYTLG" was manufactured by inserting the recombinant polynucleotide sequence of SEQ ID NO: 1 into pET His6 ProteinG TEV ligation-independent cloning (LIC) cloning vector.

The expression vector of the present disclosure can be introduced into a host cell capable of expressing the recombinant protein of the present disclosure, such as an *Escherichia coli* (*E. coli*) cell, and then the protein can be expressed in large quantities in the host cell, such as an *E. coli*, and the expressed recombinant protein for a fluorescent bio-sensor of the present disclosure can be purified by protein purification methods known in the art. According to an embodiment of the present disclosure, the recombinant protein of the present disclosure was manufactured through column chromatography using a histidine-tag (His-tag).

The recombinant protein for a fluorescent bio-sensor of the present disclosure can measure the oxidation degree of the methionine residue of a target protein by the principle described above, and the present disclosure can provide a fluorescent bio-sensor capable of measuring the oxidation degree of a methionine residue of a target protein, including a recombinant protein for a fluorescent bio-sensor.

The fluorescent bio-sensor of the present disclosure can use a recombinant protein to bind to a target protein of detection to which an antibody is strongly bound without affecting other biological activities, the protein to be detected or a sample including the protein to be detected can be treated on a substrate, immobilized on the substrate, and analyzed.

The recombinant protein of the present disclosure includes Protein G, which binds to the Fc region of the primary antibody bound to the target protein. This characteristic is utilized to enable the recombinant protein for a fluorescent bio-sensor of the present disclosure to specifically bind to a specific target protein and measure the oxidative degree of methionine residues in the target protein.

In addition, the present disclosure can provide a composition for quantitative detection of the oxidation degree of a methionine residue of a target protein, including a recombinant protein for a fluorescent bio-sensor and a primary antibody against the target protein to be detected.

In addition, the present disclosure can provide a method of measuring the oxidation degree of a methionine residue of a target protein using a recombinant protein for a fluorescent bio-sensor of the present disclosure, the method preferably including: (1) preparing a sample including a target protein including a methionine residue; (2) treating the sample with a primary antibody against the target protein to bind the antibody to the target protein; (3) treating the sample with a recombinant protein for a fluorescent bio-sensor of the present disclosure; and (4) measuring the fluorescence spectral value of the recombinant protein for a fluorescent bio-sensor.

In particular, the present disclosure is a technique capable of measuring the oxidation degree in a single protein to be analyzed, unlike conventional methods, and according to an embodiment of the present disclosure, it has been experimentally confirmed that by using the recombinant protein for a fluorescent bio-sensor of the present disclosure on proteins with varying amounts of methionine, the degree of methionine oxidation in each protein can be quantitatively measured.

In another embodiment of the present disclosure, after inducing a high level of oxidation compared to the wild type by knocking out the methionine sulfoxide reductase B1 (MsrB1) gene, various tissues (small intestine, large intestine, brain, heart, liver, kidney, and lung) were isolated from the mice, after arbitrarily choosing calmodulin as the target protein for the tissue extracts and wild-type control group, and a primary antibody against calmodulin was treated first to bind the antibody to the calmodulin protein. Then, the recombinant protein for a fluorescent bio-sensor of the present disclosure was treated, and the degree of methionine oxidation in the target protein, calmodulin, was measured by measurement of the fluorescence spectrum value by enzyme-linked immunosorbent assay (ELISA).

As a result, it was confirmed that the oxidation degree of methionine in the target protein could be quantitatively measured using the recombinant protein of the present disclosure in tissue-derived extracts including a large amount of various proteins.

In the method of the present disclosure, the measurement of the fluorescence spectral value may be calculated using the following Equation.

$$\frac{\substack{500 \text{ nm value of the excitation spectrum} \\ \text{(fixed at 535 nm emission wavelength)}}}{\substack{415 \text{ nm value of the excitation spectrum} \\ \text{(fixed at 535 nm emission wavelength)}}} = F_{500nm}/F_{415nm} \qquad \text{Equation}$$

As more oxidation occur at the methionine residue in the target protein, the lower the fluorescence spectrum value.

According to an embodiment of the present disclosure, it was confirmed that the fluorescence spectrum value can be calculated through Equation under optimal conditions for accurately measuring the degree of methionine oxidation of a specific protein through fluorescence measurement using the recombinant protein for a fluorescent bio-sensor of the present disclosure.

Furthermore, the recombinant protein for a fluorescent bio-sensor of the present disclosure can be used for the diagnosis of oxidative stress-related diseases.

Oxidative stress, such as reactive oxygen species (ROS), is a cause of various diseases. Therefore, the recombinant protein for a fluorescent bio-sensor of the present disclosure can measure the oxidation degree in the target protein, which is useful for determining the degree of symptoms of oxidative stress-related diseases, prognosis after drug treatment, or screening for therapeutic agents.

Therefore, the present disclosure may provide a method of providing information for diagnosing an oxidative stress-related disease using a recombinant protein for a fluorescent bio-sensor, the method including the processes of treating a biological sample isolated from a subject with a recombinant protein for a fluorescent bio-sensor of the present disclosure, and then comparing a fluorescence spectral value of the recombinant protein for a fluorescent bio-sensor with a fluorescence spectral value of a control group, wherein the fluorescence spectral value is calculated by Equation.

At this point, if the fluorescence spectrum value is higher than the value of the control group, it can be determined that the symptoms of the oxidative stress-related disease are improving, however, if the fluorescence spectrum value is lower than the value of the control group, it can be determined that the symptoms of the oxidative stress-related disease are worsening due to an increase in the degree of methionine oxidation in the target protein due to an increase in oxidative stress.

The sample may be cells, tissue, blood, plasma, serum, saliva, or urine.

The oxidative stress-related diseases may be selected from a group consisting of, but not limited to, cancer, stroke, myocardial infarction, angina pectoris, arteriosclerosis, infertility, hepatitis, osteoarthritis, cataracts, lipid metabolic syndrome, heart failure, hypertensive heart disease, arrhythmia, and aging.

In addition, the present disclosure can also provide a method of screening therapeutics for oxidative stress-related diseases using a recombinant protein for a fluorescent bio-sensor of the present disclosure, the method including: (1) inducing oxidative stress to a sample including a protein including a methionine residue; (2) treating the sample with a candidate drug; and (3) treating the candidate compound-treated sample with a recombinant protein for a fluorescent bio-sensor of the present disclosure, and comparing the fluorescence spectral value of the recombinant protein for a fluorescent bio-sensor with the fluorescence spectral value of a control group not treated with the candidate drug, wherein the fluorescence spectral value is calculated by Equation.

If the value of the fluorescent spectrum after treating the candidate drug is higher than the fluorescent spectrum value of the control group, the candidate drug can be considered as a therapeutic agent for oxidative stress-related disease. This means that the degree of methionine oxidation in the target protein is reduced due to the treatment of the candidate drug compared to the control group, and therefore the candidate compound can be determined to have activity to prevent, ameliorate or treat symptoms of oxidative stress.

MODE OF DISCLOSURE

Hereinafter, the present disclosure will be described in more detail through examples. These examples are intended to show the present disclosure more specifically, and the scope of the present disclosure is not limited to these examples.

Example 1

Manufacture of Recombinant DNA Structure for a Fluorescent Protein Sensor Capable of Quantitatively Measuring the Degree of Oxidation of Methionine Residues in a Specific Protein
<1-1> Manufacture of Recombinant DNA Structure for a Fluorescent Protein Sensor To manufacture the recombinant deoxyribonucleic acid (DNA) structure for a fluorescent protein sensor capable of quantitatively measuring the oxidation degree at methionine residues of a target protein, the inventors of the present application performed cloning in the following manner.

First, the pBYTLG recombinant vector of FIG. 1 was manufactured by cloning the DNA sequence encoding a yeast-derived methionine sulfoxide reductase B (MsrB) protein (1 bp to 417 bp of SEQ ID NO. 1), a circularly permuted yellow fluorescent protein (cpYFP) (418 bp to 1143 bp of SEQ ID NO. 1), a yeast-derived thioredoxin 3 (Trx3) (1144 bp to 1464 bp of SEQ ID NO. 1), a linker protein (1465 bp to 1563 bp of SEQ ID NO. 1), and a Protein G (1564 bp to 1725 bp of SEQ ID NO. 1) into pET His6 ProteinG TEV ligation-independent cloning (LIC) cloning vector.

More specifically, to clone the gene for MsrB-cpYFP-Trx3 included in the recombinant vector, polymerase chain reaction (PCR) was performed using MetROx in the pGEX4T-1 plasmid as a template, in this process, sterile water, 10×PCR buffer, deoxyribonucleoside triphosphates (dNTPs), MgSO4, MetROx forward primer, MetROx reverse primer, template DNA, and KOD FX Neo polymerase were added in sequence to a 0.2 mL PCR tube, mixed, and then spun down in a centrifuge at 100×g for 3 seconds to keep the tube walls free of solution. PCR was performed using KOD FX Neo polymerase, and the PCR reaction conditions were 94° C. for 2 minutes followed by 30 cycles of 94° C. for 20 seconds, 59° C. for 30 seconds, 68° C. for 2 minutes and 30 seconds, and then a 5 minute elongation reaction at 68° C. After PCR amplification, the gene of the linker protein and the gene of *Streptococcus*-derived Protein G were cloned into the amplification product, and the recombinant plasmid was manufactured by cloning into the multiple cloning site (MCS) of the pET His6 TEV LIC cloning vector. The recombinant vector manufactured by this method was named "pBYTLG" vector, and it was confirmed by sequencing that the DNA to be inserted was well introduced.

<1-2> Purification of Recombinant Protein for a Fluorescent Bio-Sensor

Using the "pBYTLG" expression vector manufactured in <1-1>, a recombinant protein for a fluorescent bio-sensor capable of quantitatively measuring the oxidation degree of methionine residues of a specific protein according to the present disclosure was purified by the following method.

The "pBYTLG" expression vector manufactured in <1-1> was introduced into *E. coli* to transform it, after inducing the expression of the protein in *E. coli*, the protein was purified by performing affinity chromatography using a histidine-tag (His-tag). Specifically, after transformation of the pBYTLG vector into the prepared *E. coli*, 6 L of *E. coli* culture cell solution was centrifuged to precipitate *E. coli* bodies, which were then dissolved in 100 ml of lysis buffer (20 mM Tris-HCl, 150 mM NaCl, 2 mM beta mercaptoethanol, pH8) was added to lysis, sonicated at 4° C., and then centrifuged at 14000×g to obtain the supernatant, which was subsequently filtered through a 0.45 um filter, the protein to be isolated was bound to the resin by reacting with the nickel-nitrilotriacetic acid (Ni-NTA) resin at a rate of 3 ml per minute. Then, the protein was eluted using an elution buffer (20 mM Tris-HCl, 150 mM NaCl, 2 mM beta mercapto-ethanol, 500 mM Imidazole, pH8) with 0-500 mM imidazole flowing through the concentration gradient. The eluted protein was concentrated using a 50 ml centrifugal filter, and then sodium dodecyl sulfate-polyacrylamide gel electrophoresis (SDS-PAGE) was performed using a 12 polyacrylamide gel to confirm the presence of the protein, and the amino acid sequence of the recombinant protein for a fluorescent bio-sensor of the present disclosure is shown in Sequence Listing 2.

Example 2

Confirmation of the Operation of the Fluorescent Bio-Sensor of the Present Disclosure and Analysis of its Fluorescent Properties After diluting the recombinant protein for a fluorescent bio-sensor of the present disclosure purified in Example 1 to a concentration of 10 μM, dithiothreitol (DTT), a substance that reduces disulfide bonds, is treated to a concentration of 10 mM (final concentration) and was incubated at room temperature for 30 minutes to bring the recombinant protein for a fluorescent bio-sensor of the present disclosure to a fully reduced state. Afterwards, desalting was performed using desalting columns to remove substances affecting the disulfide bond, leaving only the recombinant protein for a fluorescent bio-sensor. The reduced recombinant protein was diluted again to a concentration of 1 μM, then the absorbance spectrum was measured.

Thereafter, the reduced form of the recombinant protein for a fluorescence bio-sensor was each treated with oxidized methionine-containing protein and non-oxidized methionine-containing protein as substrates, and the fluorescence spectrum was measured after incubation at room temperature for 30 minutes. To measure the emission spectrum, the emission spectrum was measured by excitation at 410 nm, which is the highest absorbance wavelength value. Based on the result of emission spectrum, 535 nm was selected as the emission value, and then the excitation spectrum was measured.

As a result, FIGS. 3A-3D show the results of absorbance spectrum (FIG. 3A), emission spectrum (FIG. 3B), and excitation spectrum (FIG. 3C) of the recombinant protein for a fluorescent bio-sensor of the present disclosure. The analysis of the absorbance spectrum shows that the recombinant protein for a fluorescent bio-sensor of the present disclosure absorbs light in the 410 nm and 500 nm wavelengths at the highest rate in the visible region (see FIG. 3A), which indicates that the chromophore within the recombinant protein for a fluorescent bio-sensor has two stable conformations in terms of energy levels. Based on the analysis of the emission spectrum using the excitation light at 410 nm, which showed the highest absorbance, it was confirmed that the highest light emission occurred at a wavelength of 535 nm (refer to FIG. 3B). This supports the characteristic yellow fluorescence of the bio-sensor observed by the naked eye.

In addition, to confirm how the chromophore present in the recombinant for a fluorescent bio-sensor is affected by the disulfide bond between methionine sulfoxide reductase B1 (MsrB1) and thioredoxin 3 (Trx3), excitation spectrum were measured for the oxidized fluorescent bio-sensor protein with the disulfide bond formed and the reduced fluorescent bio-sensor protein without the disulfide bond formed.

As a result, there was no change in the excitation spectrum between the oxidized and reduced forms of the recombinant protein for a fluorescent bio-sensor for wavelengths shorter than 445 nm (especially at 415 nm and 442 nm). However, for wavelengths longer than 445 nm, the value of the excitation spectrum was higher in the reduced form of the recombinant protein for a fluorescent bio-sensor compared to the oxidized form of the recombinant protein for a fluorescent bio-sensor (see FIG. 3C).

These results indicate that among the two stable states of the chromophore present inside the recombinant protein for a fluorescent bio-sensor of the present disclosure, the state of the chromophore absorbing 410 nm is not affected by the disulfide bond between MsrB1 and Trx3 proteins, but the state of the chromophore absorbing 500 nm is affected by the disulfide bond between MsrB1 and Trx3 proteins. It was discovered, that when the excitation spectrum was measured with a wavelength of 535 nm as the emission wavelength, the value of the 500 nm wavelength normalized to 415 nm (F500 nm/F415 nm) could be used as a measurement index of the oxidation degree of the fluorescent bio-sensor including the recombinant protein for a fluorescent bio-sensor of the present disclosure (see FIG. 3D and FIG. 3C). In addition, it was found that as the formation of disulfide bonds between MsrB1 and Trx3 within the recombinant protein for a fluorescent bio-sensor of the present disclosure increased, the F500 nm/F415 nm value exhibited a decreasing trend.

Example 3

Analysis of the Detection Ability of the Oxidation State of Methionine in a Specific Protein Containing Purified Methionine Using the Fluorescent Bio-Sensor of the Present Disclosure.

The following experiments were performed to confirm whether the recombinant protein for a fluorescent bio-sensor manufactured in the present disclosure can be used to quantitatively measure the oxidation degree of methionine for certain protein including methionine. For the 5 types of proteins listed in Table 1 with different amounts of methionine, pure and refined proteins were prepared for each type, then, for each protein, different concentrations of hydrogen peroxide, 0 and 40 mM, were used to prepare different degrees of oxidation of methionine included in the protein. The protein oxidation process using hydrogen peroxide was performed by mixing each of the 5 purified proteins (10 μM, 100 μl) and hydrogen peroxide (0, 60 mM, 200 μl) in one tube and stirring them at room temperature for 2 hours to allow oxidation. After the oxidation reaction was completed, residual hydrogen peroxide was removed by centrifugation using an Amicon Ultra 0.5 centrifugal filter with a 10K cutoff (Millipore, USA). Each protein was quantified using the bicinchoninic acid (BCA) method and diluted to the same concentration. The dilution buffer used was a coating buffer (200 mM sodium carbonate/bicarbonate, pH9.4) to make the proteins negatively charged. The diluted protein samples were added to a Black immunoplate (SPL, Korea) and stirred for 2 hours at room temperature to allow the protein sample to adhere to the positively charged plate bottom. To the coated plate, 200 μl of wash buffer (2 weight/volume (w/v) bovine serum albumin (BSA), 20 mM Phosphate, 150 mM NaCl, 0.05 volume/volume (v/v) Tween 20, pH7.4) including 2 BSA was added, and then the plate was incubated for 1 hour at room temperature to coat the uncoated portion of the plate with non-reactive BSA protein (see FIG. 2C). After that, primary antibodies for each protein were added to the wash buffer containing 2 BSA, at a volume of 100 μl per protein, and was incubated at room temperature for 2 hours to allow the antibodies to bind to the protein. Thereafter, the unbound antibodies were removed through washing, the recombinant protein for the methionine fluorescent bio-sensor of the present disclosure was then added to each sample at a concentration of 1 μM, with 100 μl added to each sample, and incubated for 2 hours at 18° C., allowing the Protein G portion of the recombinant protein for a fluorescence bio-sensor of the present disclosure to bind to the fragment crystallizable (Fc) region of the primary antibody. Thereafter, the unbound recombinant proteins for a fluorescent bio-sensor were removed through washing, the samples were incubated at 37° C. for 30 minutes. The emission wavelength was fixed at 535 nm, and the excitation spectrum was measured.

Figure 4:
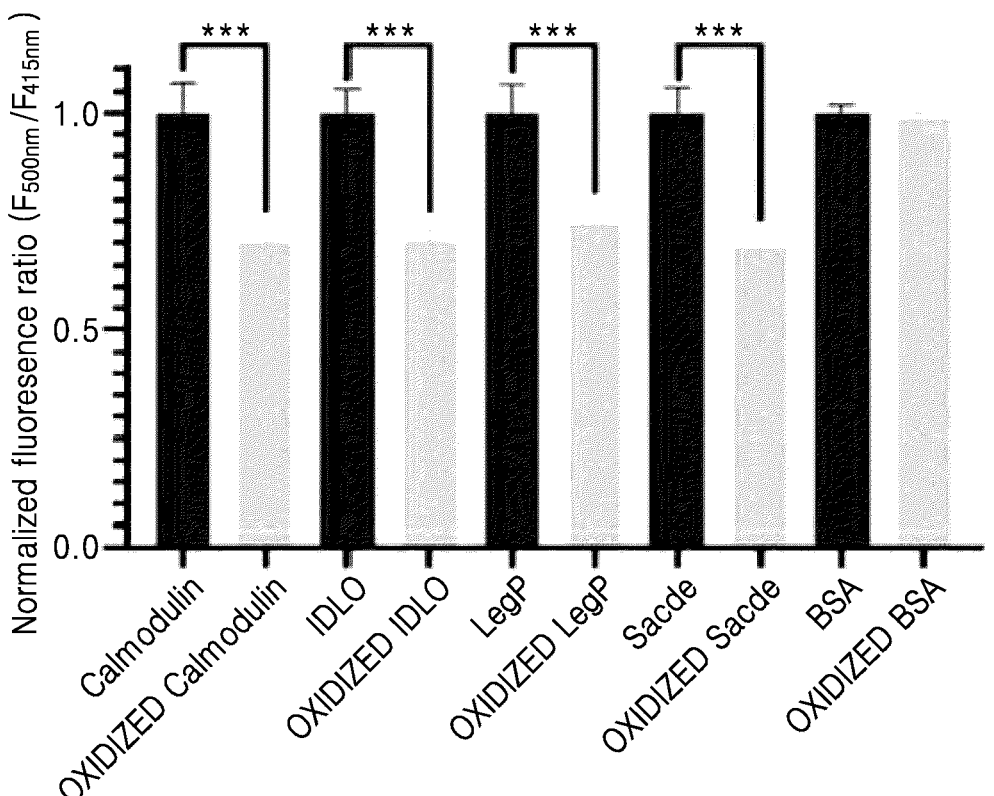
FIG. 4 shows the results of measuring a methionine oxidation state of each specific protein present in a mixed biological sample using a recombinant protein for a fluorescent bio-sensor of the present disclosure against a methionine-containing protein, and the resulting values ($F_{500\ nm}/F_{415\ nm}$) of the excitation spectrum measured by ELISA by using the recombinant protein for a fluorescent bio-sensor of the present disclosure for each protein.
Figure 5A:
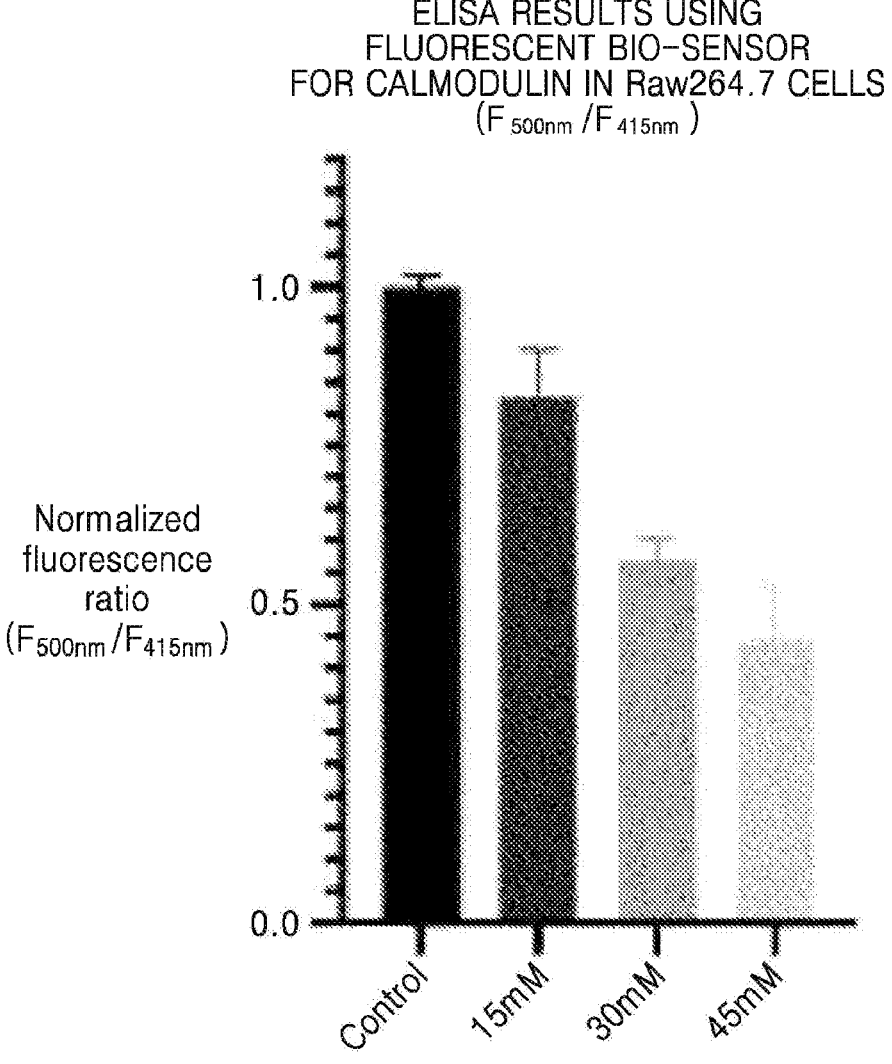
Figure 5B:
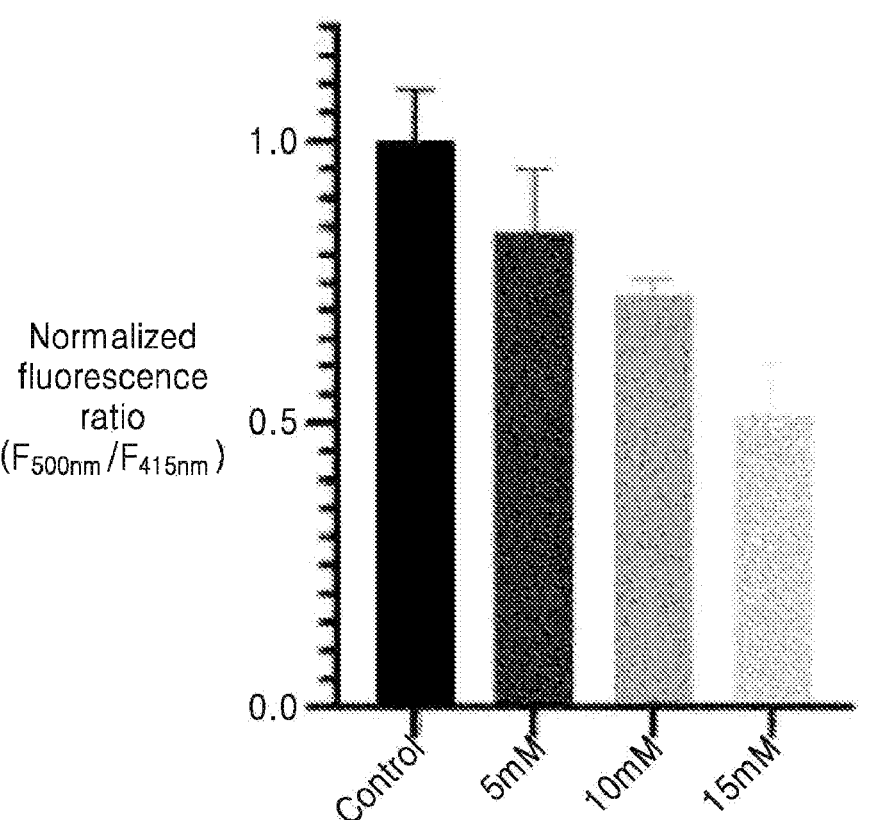
Figure 5C:
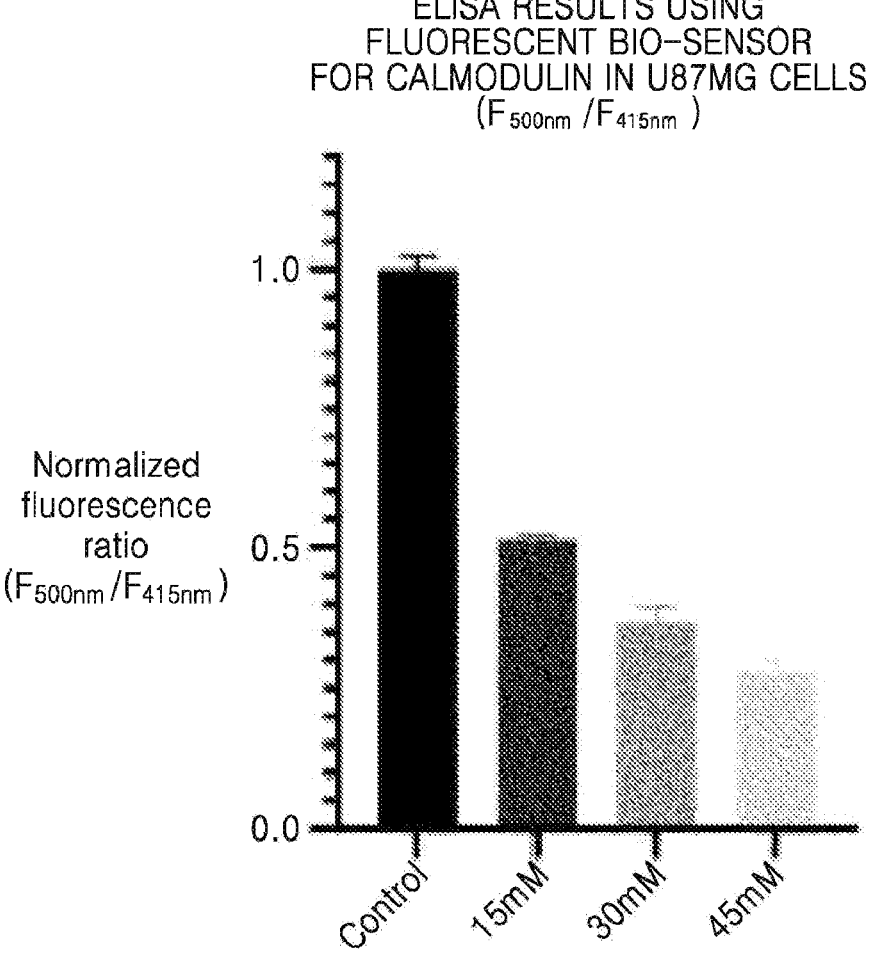
Figure 5D:
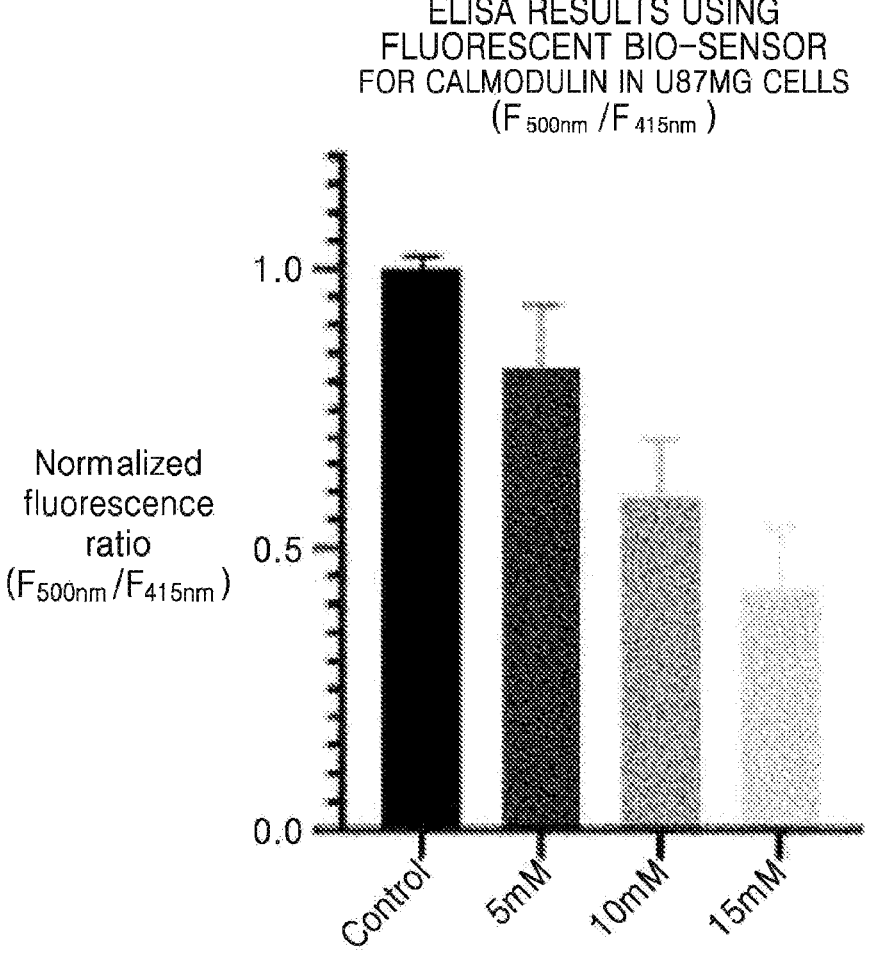

As a result, in FIG. 4, the analyzed results are shown as the normalized value of the 500 nm excitation spectrum to the 415 nm excitation spectrum based on the excitation spectra obtained for the samples described above. Among the five types of proteins with different methionine contents, for the four proteins with higher methionine content, the $F_{500\ nm}/F_{415\ nm}$ value was measured to be lower in the sample oxidized with 40 mM hydrogen peroxide. In contrast, for the protein BSA, which has a low methionine content, there was no significant difference in the $F_{500\ nm}/F_{415\ nm}$ values between the samples oxidized with 40 mM hydrogen peroxide and those that did not undergo the oxidation process.

These results show that when the methionine residue in the protein used as a substrate is oxidized, the recombinant protein for a fluorescent bio-sensor of the present disclosure can reduce it while becoming oxidized itself. This forms a disulfide bond between methionine sulfoxide reductase B (MsrB1) and thioredoxin 3 (Trx3) within the recombinant protein, resulting in a decrease in $F_{500\ nm}/F_{415\ nm}$ (FIG. 2B) Therefore, when using the recombinant protein for a fluorescent bio-sensor of the present disclosure for a specific protein whose methionine residues are oxidized, it is possible to quantitatively measure the degree of oxidation of methionine residues in individual specific proteins.

Example 4

Analysis of the Detection Capability of Methionine Oxidation States in Specific Proteins Using the Fluorescent Bio-Sensor of the Present Disclosure in Mice Organ Extracts Furthermore, the inventors of the present application conducted experiments to confirm whether the recombined protein for a fluorescent bio-sensor of the present disclosure can quantitatively measure the degree of methionine oxidation in individual specific proteins in extracts from organs inside the body using mice organ extracts.

The enzyme methionine sulfoxide reductase B1 (MsrB1) plays a role in methionine reduction by reducing methionine sulfoxide when methionine residues in proteins are oxidized to methionine sulfoxide. MsrB1 knock-out (MsrB1$^{-/-}$) mice, which are mice with a genetic deficiency in the MsrB1 enzyme, generally have higher levels of oxidized methionine residues in proteins compared to wild-type (WT) mice. Analysis was conducted to determine whether the fluorescent bio-sensor of the present disclosure can measure the oxidation state of methionine residues in a specific protein, calmodulin, in organs of MsrB1$^{-/-}$ mice and WT mice.

For this purpose, 10-week-old MsrB1–/– mice and WT mice were prepared from the C57BL/6J mouse strain, and mice calmodulin was selected as the target protein for measuring the degree of methionine oxidation. Then, seven organs (small intestine, large intestine, brain, heart, liver, kidney, and lung) with high expression levels of calmodulin

TABLE 1

| Protein | Organism | Accession number | Total amino acids | # of Met residues | % of Met |
|---|---|---|---|---|---|
| Calmodulin-2 isoform 1(Calmodulin) | *Mus musculus* | NP_031615.1 | 149 | 10 | 7 |
| Hypothetical protein(IDLO) | *Idiomarina loihiensis* | WP_011234467.1 | 147 | 32 | 22 |
| Hypothetical protein(LegP) | *Legionella pneumophila* | WP_010946790.1 | 146 | 37 | 25 |
| Hypothetical protein (Sacde) | *Saccharophagus degradans* | WP_011468416.1 | 146 | 36 | 25 |
| Serum albumin precursor(BSA) | *Bos Taurus* | NP_851335.1 | 607 | 5 | 1 |

15

16 protein were isolated. Each organ was washed with PBS solution, and then 2 mL of 0.2% Tween/50 mM Tris-base saline solution was added. The tissue and cells were homogenized using a homogenizer and then centrifuged to obtain organ-specific extracts. Then, by using the same method as described in the example above, the oxidation state of methionine residues in calmodulin protein was measured using enzyme-linked immunosorbent assay (ELISA) experiments with a recombinant protein for a fluorescent bio-sensor of the present invention.

Figure 6:
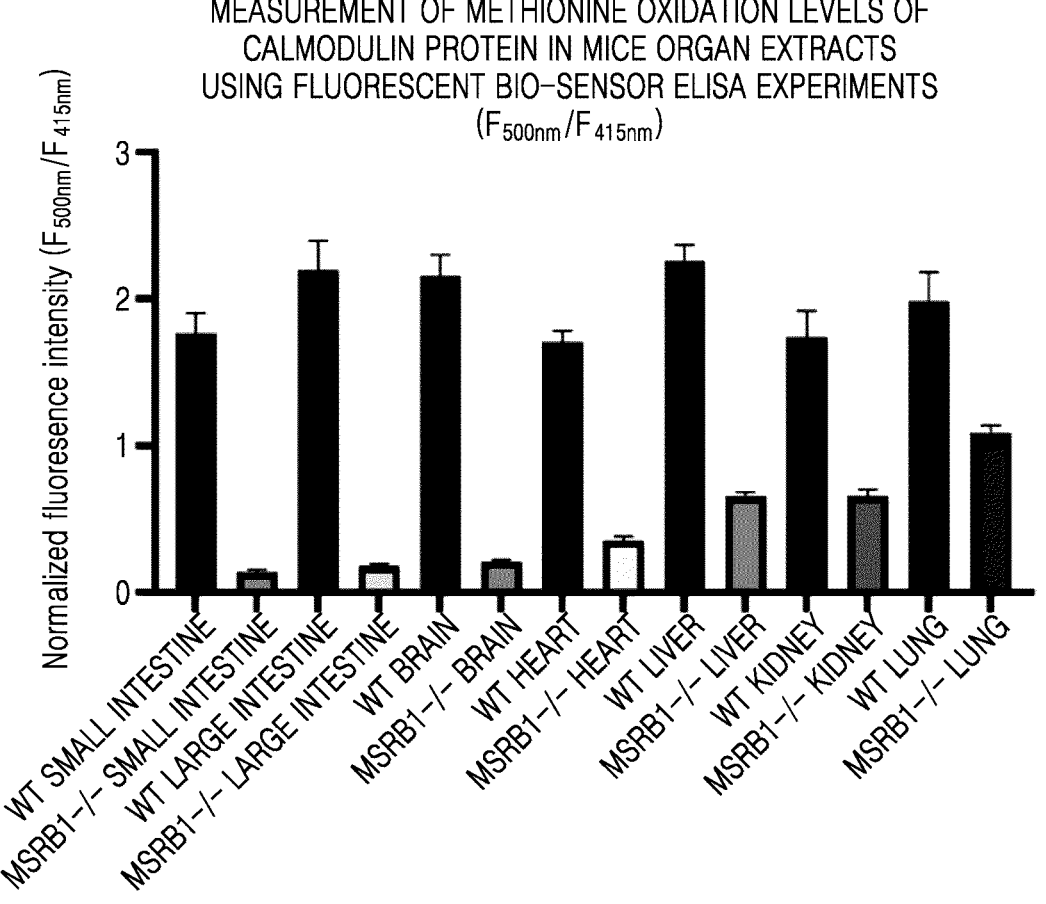
FIG. 6 shows the results of an ELISA experiment in which a recombinant protein for a fluorescent bio-sensor of the present disclosure was used on a mice organ extract, the results showing the excitation spectrum ($F_{500\ nm}/F_{415\ nm}$) result values of the fluorescent bio-sensor of the present disclosure measured when calmodulin, one of the methionine-containing proteins, was used as a target protein.

As a result, FIGS. 5A-5D show the values obtained by normalizing the excitation spectrum value of 500 nm to the excitation spectrum of 415 nm based on the result of the excitation spectrum for the sample. For all seven organs tested in the present disclosure, the $F_{500\ nm}/F_{415\ nm}$ values of the recombinant protein for a fluorescent bio-sensor of the present disclosure were found to be lower in MsrB1$^{-/-}$ mice compared to WT mice (see FIG. 6).

This means that the oxidation state of the calmodulin protein is higher in MsrB1$^{-/-}$ mice than in WT mice, indicating that the methionine residues of the protein are oxidized to a higher level in the absence of MsrB1, an enzyme that reduces methionine residues in protein.

Therefore, based on these results, the inventors of the present application were able to determine that by using the recombinant protein for a fluorescent bio-sensor and a fluorescent bio-sensor using the recombinant protein for a fluorescent bio-sensor of the present disclosure, it is possible to quantitatively measure the oxidation degree of methionine of a specific protein of interest.

So far, the present disclosure has been looked at with respect to its preferred examples. One of ordinary skill in the art to which the present disclosure belongs will understand that the present disclosure may be implemented in modified forms without departing from the fundamental characteristics of the present disclosure. Therefore, the disclosed examples should be considered from an illustrative rather than a limiting perspective. The scope of the present disclosure is defined by the claims rather than the foregoing description, and any variations within the scope of the claims will be construed as being included within the present disclosure.

The invention claimed is:

1. A recombinant protein for a fluorescent bio-sensor configured to measure a degree of oxidation of methionine residues in a target protein, the recombinant protein comprising:
   methionine sulfoxide reductases B (MsrB) protein; circularly permuted yellow fluorescence protein (cpYFP); thioredoxin 3 protein; linker protein; and protein G, which are sequentially linked, wherein the linker protein consists of 489th to 521st amino acids of an amino acid sequence of SEQ ID NO: 2.

2. The recombinant protein of claim 1, wherein the recombinant protein consists of the amino acid sequence of SEQ ID NO: 2.

3. A polynucleotide encoding the recombinant protein of claim 1.

4. The polynucleotide of claim 3, wherein the polynucleotide consists of the nucleotide sequence of SEQ ID NO: 1.

5. An expression vector comprising the polynucleotide of claim 3.

6. A transformant transformed with the expression vector of claim 5.

7. A fluorescent bio-sensor for measuring a degree of oxidation of methionine residues of a target protein, comprising the recombinant protein of claim 1.

8. A quantitative detection composition for measuring a degree of oxidation of methionine residues in a target protein, the quantitative detection composition comprising: the recombinant protein of claim 1, and a primary antibody for a target protein to be detected.

9. A method of measuring a degree of oxidation of methionine residues in a target protein, comprising:

(1) preparing a sample comprising a target protein comprising methionine residues;

(2) treating the sample with a primary antibody against the target protein to bind the primary antibody to the target protein;

(3) treating the recombinant protein for a fluorescent bio-sensor of claim 1; and (4) measuring a fluorescence spectrum value of the recombinant protein for a fluorescent bio-sensor.

10. The method of claim 9, wherein the measurement of the fluorescence spectrum value is calculated using the following Equation.

$$\frac{\text{500 nm value of the excitation spectrum (fixed at 535 nm emission wavelength)}}{\text{415 nm value of the excitation spectrum (fixed at 535 nm emission wavelength)}} = F_{500\,nm}/F_{415\,nm} \quad \text{Equation}$$

11. The method of claim 10, wherein the greater the oxidation of methionine residues in the target protein, the lower a numerical value of the fluorescence spectrum value is.

12. A method of providing information for diagnosis of oxidative stress-related diseases, the method comprising treating a biological sample isolated from a test subject with the composition of claim 8, and then comparing a fluorescence spectrum value of a recombinant protein for a fluorescence bio-sensor with a fluorescence spectrum value of a normal control group, wherein the fluorescence spectrum value is calculated by the following Equation.

$$\frac{\text{500 nm value of the excitation spectrum (fixed at 535 nm emission wavelength)}}{\text{415 nm value of the excitation spectrum (fixed at 535 nm emission wavelength)}} = F_{500\,nm}/F_{415\,nm} \quad \text{Equation}$$

13. The method of claim 12, wherein the sample is a cell, tissue, blood, plasma, serum, saliva, or urine.

14. The method of claim 12, wherein the oxidative stress-related diseases are selected from the group consisting of cancer, stroke, myocardial infarction, angina, arteriosclerosis, infertility, hepatitis, osteoarthritis, cataracts, lipid metabolic disease, heart failure, hypertensive heart disease, arrhythmia, and aging.

15. A method of screening for a therapeutic agent for an oxidative stress-related disease, the method comprising:

(1) inducing oxidative stress in a sample comprising a protein containing methionine residues;

(2) treating the sample with a candidate drug; and (3) treating the candidate substance-treated sample with the composition of claim 8, and comparing a fluorescence spectrum value of a recombinant protein for a fluorescent bio-sensor with a fluorescence spectrum value of a control group not treated with the candidate drug, wherein the fluorescence spectrum value is calculated by the following Equation.

$$\frac{\text{500 nm value of the excitation spectrum (fixed at 535 nm emission wavelength)}}{\text{415 nm value of the excitation spectrum (fixed at 535 nm emission wavelength)}} = F_{500\,nm}/F_{415\,nm} \quad \text{Equation}$$

16. The method of claim 15, further comprising determining the candidate drug as a therapeutic agent for an oxidative stress-related disease, when the fluorescence spectrum value of treatment with the candidate drug is greater than the fluorescence spectrum value of the control group.

17. The method of claim 15, wherein the oxidative stress-related disease is selected from the group consisting of cancer, stroke, myocardial infarction, angina pectoris, arteriosclerosis, infertility, hepatitis, osteoarthritis, cataracts, lipid metabolic syndrome, heart failure, hypertensive heart disease, arrhythmia, and aging.

* * * * *

SEQUENCE LISTING

```
<160> NUMBER OF SEQ ID NOS: 2

<210> SEQ ID NO 1
<211> LENGTH: 1725
<212> TYPE: DNA
<213> ORGANISM: Artificial Sequence
<220> FEATURE:
<223> OTHER INFORMATION: Polynucleotide sequence encoding the
      recombinant protein for fluorescent biosensor of the present
      invention

<400> SEQUENCE: 1
aagagcaaga aaatgagtga cgaatcgaat gacgtgaagt ggaacgatgc cctgacacca      60
ttgcagctga tggtgctgag agataaggcc actgaaaggc ccaacaccgg tgcgtattta     120
cacaccaacg agtccggtgt ctaccattgt gccaactgcg acagaccgtt gtattcgagc     180
aaggccaagt tcgacgctcg ttgtggatgg cccgcattct acgaagaggt atcccctgga     240
gccatcacat atcatcgtga caattcttta atgcctgcga gggtggagat atgttgtgca     300
aggtgtggtg gacacttggg acatgtgttt gaaggtgaag gctggaaaca gttgctaaac     360
ttgcccaagg acaccagaca ctgtgtgaac agtgcgtctt taaacctcaa gaaggataac     420
gtctatatca tggccgacaa gcagaagaac ggcatcaagg ccaacttcaa gatccgccac     480
aacgtcgagg acggcagcgt gcagctcgcc gaccactacc agcagaacac ccccatcggc     540
gacggccccg tgctgctgcc cgacaaccac tacctgagct tccagtccgt cctgagcaaa     600
gaccccaacg agaagcgcga tcacatggtc ctgctggagt tcgtgaccgc cgccgggatc     660
actctcggca tggacgagct gtacaacgtg gatggcggta gcggtggcac cggcagcaag     720
ggcgaggagc tgttcaccgg ggtggtgccc atcctggtcg agctggacgg cgacgtaaac     780
ggccacaagt tcagcgtgtc cggcgagggc gagggcgatg ccacctacgg caagctgacc     840
ctgaagctga tctgcaccac cggcaagctg cccgtgccct ggcccaccct cgtgaccacc     900
ctcggctacg gcctgaagtg cttcgcccgc tacccccgacc acatgaagca gcacgacttc     960
ttcaagtccg ccatgcccga aggctacgtc caggagcgca ccatcttctt caaggacgac    1020
ggcaactaca gacccgcgc cgaggtgaag ttcgagggcg acaccctggt gaaccgcatc    1080
gagctgaagg gcatcggctt caaggaggac ggcaacatcc tggggcacaa gctggagtac    1140
```

-continued

```
aacatgtcct catacaccag tattactaaa ttgacgaacc taacagaatt taggaatttg    1200
atcaagcaaa atgataaact agtcatcgat ttttatgcta cttggtgtgg cccctctaag    1260
atgatgcaac cacacttaac gaaattaatt caggcttatc cagatgtaag atttgtcaag    1320
tgcgacgtgg acgaatcacc agatattgcc aaagagtgtg aagtgacggc tatgcccacc    1380
tttgttcttg gcaaggatgg ccaactcatc ggcaagatca ttggagctaa ccctactgct    1440
ttagagaagg gaatcaaaga tctactggca gaggcagccg ccaaggaagc ggctgctaaa    1500
gaagcagcag ctaaagaagc ggccgcgaaa gcggcggctg ccatggttc ttctatgact     1560 acttacaaat taatccttaa tggtaaaaca ttgaaaggcg aaacaactac tgaagctgtt    1620
gatgctgcta ctgcagaaaa agtcttcaaa caatacgcta acgacaacgg tgttgacggt    1680
gaatggactt acgacgatgc gactaagacc tttacagtta ctgaa                     1725
```

```
<210> SEQ ID NO 2
<211> LENGTH: 575
<212> TYPE: PRT
<213> ORGANISM: Artificial Sequence
<220> FEATURE:
<223> OTHER INFORMATION: Recombinant protein sequence for fluorescent
      biosensor of the present invention

<400> SEQUENCE: 2

Lys Ser Lys Lys Met Ser Asp Glu Ser Asn Asp Val Lys Trp Asn Asp
1               5                   10                  15

Ala Leu Thr Pro Leu Gln Leu Met Val Leu Arg Asp Lys Ala Thr Glu
                20                  25                  30

Arg Pro Asn Thr Gly Ala Tyr Leu His Thr Asn Glu Ser Gly Val Tyr
            35                  40                  45

His Cys Ala Asn Cys Asp Arg Pro Leu Tyr Ser Ser Lys Ala Lys Phe
        50                  55                  60

Asp Ala Arg Cys Gly Trp Pro Ala Phe Tyr Glu Glu Val Ser Pro Gly
65                  70                  75                  80

Ala Ile Thr Tyr His Arg Asp Asn Ser Leu Met Pro Ala Arg Val Glu
                85                  90                  95

Ile Cys Cys Ala Arg Cys Gly Gly His Leu Gly His Val Phe Glu Gly
            100                 105                 110

Glu Gly Trp Lys Gln Leu Leu Asn Leu Pro Lys Asp Thr Arg His Cys
        115                 120                 125

Val Asn Ser Ala Ser Leu Asn Leu Lys Lys Asp Asn Val Tyr Ile Met
    130                 135                 140

Ala Asp Lys Gln Lys Asn Gly Ile Lys Ala Asn Phe Lys Ile Arg His
145                 150                 155                 160

Asn Val Glu Asp Gly Ser Val Gln Leu Ala Asp His Tyr Gln Gln Asn
                165                 170                 175

Thr Pro Ile Gly Asp Gly Pro Val Leu Leu Pro Asp Asn His Tyr Leu
            180                 185                 190

Ser Phe Gln Ser Val Leu Ser Lys Asp Pro Asn Glu Lys Arg Asp His
        195                 200                 205

Met Val Leu Leu Glu Phe Val Thr Ala Ala Gly Ile Thr Leu Gly Met
    210                 215                 220

Asp Glu Leu Tyr Asn Val Asp Gly Gly Ser Gly Gly Thr Gly Ser Lys
225                 230                 235                 240

Gly Glu Glu Leu Phe Thr Gly Val Val Pro Ile Leu Val Glu Leu Asp
            245                 250                 255
```

-continued

```
Gly Asp Val Asn Gly His Lys Phe Ser Val Ser Gly Glu Gly Glu Gly
            260             265             270

Asp Ala Thr Tyr Gly Lys Leu Thr Leu Lys Leu Ile Cys Thr Thr Gly
            275             280             285

Lys Leu Pro Val Pro Trp Pro Thr Leu Val Thr Thr Leu Gly Tyr Gly
            290             295             300

Leu Lys Cys Phe Ala Arg Tyr Pro Asp His Met Lys Gln His Asp Phe
305             310             315             320

Phe Lys Ser Ala Met Pro Glu Gly Tyr Val Gln Glu Arg Thr Ile Phe
                325             330             335

Phe Lys Asp Asp Gly Asn Tyr Lys Thr Arg Ala Glu Val Lys Phe Glu
                340             345             350

Gly Asp Thr Leu Val Asn Arg Ile Glu Leu Lys Gly Ile Gly Phe Lys
            355             360             365

Glu Asp Gly Asn Ile Leu Gly His Lys Leu Glu Tyr Asn Met Ser Ser
            370             375             380

Tyr Thr Ser Ile Thr Lys Leu Thr Asn Leu Thr Glu Phe Arg Asn Leu
385             390             395             400

Ile Lys Gln Asn Asp Lys Leu Val Ile Asp Phe Tyr Ala Thr Trp Cys
                405             410             415

Gly Pro Ser Lys Met Met Gln Pro His Leu Thr Lys Leu Ile Gln Ala
                420             425             430

Tyr Pro Asp Val Arg Phe Val Lys Cys Asp Val Asp Glu Ser Pro Asp
            435             440             445

Ile Ala Lys Glu Cys Glu Val Thr Ala Met Pro Thr Phe Val Leu Gly
            450             455             460

Lys Asp Gly Gln Leu Ile Gly Lys Ile Ile Gly Ala Asn Pro Thr Ala
465             470             475             480

Leu Glu Lys Gly Ile Lys Asp Leu Leu Ala Glu Ala Ala Ala Lys Glu
                485             490             495

Ala Ala Ala Lys Glu Ala Ala Ala Lys Glu Ala Ala Ala Lys Ala Ala
            500             505             510

Ala Gly His Gly Ser Ser Met Thr Thr Tyr Lys Leu Ile Leu Asn Gly
            515             520             525

Lys Thr Leu Lys Gly Glu Thr Thr Thr Glu Ala Val Asp Ala Ala Thr
            530             535             540

Ala Glu Lys Val Phe Lys Gln Tyr Ala Asn Asp Asn Gly Val Asp Gly
545             550             555             560

Glu Trp Thr Tyr Asp Asp Ala Thr Lys Thr Phe Thr Val Thr Glu
                565             570             575
```